(12) United States Patent
Ooya et al.

(10) Patent No.: US 8,507,659 B2
(45) Date of Patent: *Aug. 13, 2013

(54) METHOD FOR CHEMICALLY MODIFYING BIOPOLYMER AND POLYPEPTIDE

(75) Inventors: Shouji Ooya, Ashigarakami-gun (JP); Tetsuo Hiratou, Ashigarakami-gun (JP); Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/745,214

(22) PCT Filed: Nov. 28, 2008

(86) PCT No.: PCT/JP2008/071611
§ 371 (c)(1),
(2), (4) Date: May 27, 2010

(87) PCT Pub. No.: WO2009/069727
PCT Pub. Date: Jun. 4, 2009

(65) Prior Publication Data
US 2010/0323421 A1 Dec. 23, 2010

(30) Foreign Application Priority Data
Nov. 28, 2007 (JP) .................. 2007-307161

(51) Int. Cl.
*C07K 14/00* (2006.01)
*C07K 14/78* (2006.01)
*C07H 1/00* (2006.01)
*C12N 9/96* (2006.01)

(52) U.S. Cl.
USPC ........... 530/402; 530/350; 530/354; 435/188; 536/123.1

(58) Field of Classification Search
USPC .............. 530/354, 402, 350; 536/124, 123.1; 435/41, 188
See application file for complete search history.

(56) References Cited

U.S. PATENT DOCUMENTS 3,097,051 A * 7/1963 Wade ................................. 8/120
4,076,870 A * 2/1978 Yamamoto .................. 427/393.2
4,745,178 A * 5/1988 DiMarchi et al. ............. 530/345
5,521,097 A * 5/1996 Uchida et al. ................... 436/86
6,645,712 B1 11/2003 Olijve et al.
6,737,072 B1 5/2004 Angele et al.
2006/0134170 A1 6/2006 Griffith et al.
2007/0100091 A1* 5/2007 Dhanabalan et al. ......... 525/480

FOREIGN PATENT DOCUMENTS

| EP | 0 364 980 A2 | 4/1990 |
|----|---|---|
| EP | 0 539 167 A2 | 4/1993 |
| EP | 0 926 543 B1 | 6/1999 |
| EP | 1 014 176 A2 | 6/2000 |
| EP | 1 398 324 A1 | 3/2004 |
| EP | 2 100 914 A1 | 9/2009 |
| JP | 04-189833 A | 7/1992 |
| JP | 05-214092 A | 8/1993 |
| JP | 2001-224677 A | 8/2001 |
| JP | 2002-531182 A | 9/2002 |
| JP | 2004-532802 A | 10/2004 |
| JP | 2004-321484 A | 11/2004 |
| JP | 2006-063283 A | 3/2006 |
| WO | 02 28437 A1 | 4/2002 |
| WO | 2004/085473 A2 | 10/2004 |
| WO | 2007 048026 A2 | 4/2007 |
| WO | 2008/072379 A1 | 6/2008 |

OTHER PUBLICATIONS

Fissi et al., Macromolecules, 32, 7116-7121 (1999).*
Zhao et al., Polymeric Materials Science and Engineering (1995), 72, 86-87.*
International Preliminary Report on Patentability and Written Opinion, corresponding to PCT/JP2008/071611, dated Jun. 8, 2010.
Extended European Search Report on EP 08854075.2 dated Jul. 21, 2011, including European Search Opinion.
Extended European Search Report dated Jul. 21, 2011 on European Application No. EP 08854075.2.
Office Action dated Nov. 5, 2012 in European Application No. 08 854 075.2.
Office Action dated May 21, 2013 in Japanese Application No. 2009-543860.

* cited by examiner

*Primary Examiner* — Chih-Min Kam
(74) *Attorney, Agent, or Firm* — Sughrue Mion, PLLC

(57) ABSTRACT

It is an object of the present invention to provide a method for chemically modifying biopolymer and polypeptide with a hydrophobic compound or a compound which causes degradation or reaction under basic condition. The present invention provides a method for producing a chemically modified biopolymer or polypeptide, wherein a biopolymer or polypeptide is chemically modified in a reaction solution containing an organic fluorine compound.

10 Claims, No Drawings

METHOD FOR CHEMICALLY MODIFYING BIOPOLYMER AND POLYPEPTIDE

The present application is a 371 of PCT/JP2008/071611, filed Nov. 28, 2008, the disclosure of which is incorporated herein by reference.

TECHNICAL FIELD

The present invention relates to an efficient method for chemically modifying biopolymer and polypeptide.

BACKGROUND ART

Biopolymers which are biologically derived macromolecules have each specific physical and biological property, and therefore are frequently used for medical and biological use. However, biopolymers are generally inferior in terms of workability and performance control as compared with synthetic polymers, and therefore biopolymers are attempted to be highly functionalized by hybridization of biopolymer and synthetic polymer or chemical modification with low molecular weight compound.

On the other hand, by development of genetic engineering, it becomes possible to artificially synthesize various proteins which are equivalent or similar to biological proteins, as well as novel proteins. In particular, a functional group which can be chemically modified can be introduced into an artificially synthesized protein. By such chemical modification of a novel protein, a protein analogue which is more highly functional can be produced. However, in such procedure, introduction of a functional group into a side chain is limited, and at present there are many functional groups which cannot be introduced.

When a side chain of biopolymer or polypeptide is chemically modified, there is generally used a method by condensation reaction using an amino group or carboxyl group in water. Namely, water soluble biopolymer or polypeptide is dissolved in water, and is reacted with a compound having a desired functional group by a condensing agent, so that a functional group is introduced into biopolymer or polypeptide (Patent document 1). It is difficult to apply this method for the introduction of poorly soluble compound. For the introduction of poorly soluble compound, there is used a method where a compound to be modified is previously dissolved in sodium hydroxide solution, and the pH of the solution is then returned to be around neutral, and the reaction is carried out in water (Non-Patent Document 1). However, it has been suggested that, in this method, high solubility cannot be achieved in the case of highly hydrophobic compound and this method cannot be applied to a compound having a functional group which causes degradation or reaction in the alkaline state.

On the other hand, proteins such as collagen or gelatin are dissolved in 1,1,1,3,3,3-hexafluoro-2-propanol (HFIP). Therefore, production of matrix for tissue construction (Patent Document 2) and production of fibrous form matrix by electrospinning (Patent Document 3 and Patent Document 4) is performed. However, these attempts are directed to the production of matrix only, and these documents neither teach nor suggest any chemical modification of protein.

Non-Patent Document 1: Journal of Biomaterial Science, Polymer Edition 16 (7) 809-827, 2005
Patent Document 1: Japanese Patent Publication (Kokai) 2001-224677
Patent Document 2: Japanese Patent Publication (Kohyo) 2002-531182
Patent Document 3: Japanese Patent Publication (Kohyo) 2004-532802
Patent Document 4: Japanese Patent Publication (Kokai) 2004-321484

DISCLOSURE OF THE INVENTION

Object to be Solved by the Invention

It is an object of the present invention to solve the above problems of conventional techniques. That is, it is an object of the present invention to provide a method for chemically modifying biopolymer and polypeptide with a hydrophobic compound or a compound which causes degradation or reaction under basic condition.

Means for Solving the Object

As a result of intensive studies in order to achieve the above objects, the present inventors have found that even a highly hydrophobic compound or a compound which causes degradation or reaction in alkali state can be efficiently introduced by chemically modifying biopolymer and polypeptide in a reaction solution containing an organic fluorine compound. This has led to the completion of the present invention.

The present invention provides a method for producing a chemically modified biopolymer or polypeptide, wherein a biopolymer or polypeptide is chemically modified in a reaction solution containing an organic fluorine compound.

Preferably, the biopolymer comprises at least one which is selected from a group consisting of a protein, a polysaccharide, and a derivative thereof.

Preferably, the biopolymer is protein.

Preferably, the biopolymer comprises at least one selected from the group consisting of collagen, gelatin, albumin, laminin, casein, fibroin, fibrin, fibronectin, vitronectin, urokinase, thrombomodulin, and antithrombin III.

Preferably, the protein is a human-, bovine-, pig-, fish or plant-derived protein, or a gene recombinant protein.

Preferably, the chemical modification is a chemical modification which is made via amide binding, ester binding, ether binding or urethane binding.

Preferably, the chemical modification is an intermolecular cross-linking reaction or an intramolecular cross-linking reaction.

Preferably, the chemical modification is an introduction of a functional group into biopolymer or polypeptide.

Preferably, the compound which is used for the chemical modification of biopolymer is a compound having carbonate ester group, epoxide group, ester group, amide group, or dithiocarbamy group.

Preferably, the chemical modification is carried out using a condensing agent.

Preferably, the chemical modification is carried out by a reaction with acid anhydride, acid chloride, or epoxide.

Preferably, the organic fluorine compound has a carbon number of 1 to 8.

Preferably, the organic fluorine compound is alcohol, or ketone.

Preferably, the organic fluorine compound is 2,2,2-trifluoroethanol, 1,1,1,3,3,3-hexafluoro-2-propanol, or hexafluoroacetone.

Preferably, the organic fluorine compound is 2,2,2-trifluoroethanol.

Effect of the Invention

By performing the present invention, (1) a more efficient reaction can be carried out as compared in the reaction in water system, (2) handling becomes easy, when a substrate such as gelatin which forms gel at low temperature in an aqueous solution is used and highly reactive reagent is used, and (3) modification with highly hydrophobic compound becomes possible. As a result, according to the present invention, various functional groups can be introduced into biopolymer or polypeptide, and biopolymer or polypeptide can be highly functionalized.

BEST MODE FOR CARRYING OUT THE INVENTION

Hereinafter, the present invention is described in greater detail.

A biopolymer (a biologically derived polymer) to be used in the present invention is not particularly limited, as long as the present invention can be realized, and it is preferably a protein, a polysaccharide or a derivative thereof, or a salt thereof. When a protein is used, any protein in a spherical form or a fibrous form can be used. The biopolymer used in the present invention may include synthetic polypeptide. More preferred examples of a biopolymer include: collagen, gelatin, albumin, laminin, casein, fibroin, fibrin, chitosan, fibronectin, vitronectin, urokinase, thrombomodulin, antithrombin III and hyaluronic acid ester. More preferably, collagen, gelatin, albumin, casein, or fibroin is used. Most preferably, collagen or gelatin is used. The protein origin is not particularly limited. Any human-, bovine-, pig-, or fish-derived proteins or gene recombinants proteins can be used. Examples of gene recombinant gelatins that can be used are those described in EP0926543B, WO2004-085473 publication, EP1398324A, EP1014176A, U.S. Pat. No. 6,645,712 or the like; however, it is not limited thereto. The biopolymer may be partially hydrolyzed.

The method for producing the polypeptide used in the present invention is not particularly limited. For example, any polypeptide which was produced in *E. coli* or yeast or any chemically synthesized polypeptide can be used.

The organic fluorine compound which is used in the present invention is not particularly limited, so long as biopolymer or polypeptide is dissolved therein, and it is preferably an organic fluorine compound having a carbon number of 1 to 8, further preferably an organic fluorine compound having a carbon number of 1 to 6, and even more preferably an organic fluorine compound having a carbon number of 1 to 3. Further preferably, such an organic fluorine compound is alcohol, ketone, or carboxylic acid. Particularly preferably, it is 1,1,1,3,3,3-hexafluoro-2-propanol (HFIP), 2,2,2-trifluoroethanol (TFE), or hexafluoroacetone. Most preferably, it is 2,2,2-trifluoroethanol. Further, the organic fluorine compound may be used singly, or may be used as a mixture with a solvent which is compatible with said organic fluorine compound.

Although the organic fluorine compound which is used in the present invention is not particularly limited, it is preferably a compound which is liquid at normal temperature. Among them it is preferably C2-C8 non-aromatic organic fluorine compound or C6-C12 aromatic fluorine-containing-esters, -carboxylic acids or -nitriles. Preferred examples of the C2-C8 non-aromatic organic fluorine compound include C2-C8 fluorine-containing alcohols, fluorine-containing amides, fluorine-containing esters, fluorine-containing carboxylic acids, and fluorine-containing ethers. The organic fluorine compound may contain an atom other than fluorine. For example, a part of the atom may be substituted with a halogen atom. Among them, more preferred compound is C2-C3 fluorine-containing alcohols. Most preferred compound is 1,1,1,3,3,3-hexafluoro-2-propanol, 2,2,2-trifluoroethanol, trifluoroacetic acid, or pentafluoropropionic acid. Such solvent is compatible with various solvents, and therefore such solvent may be used as a mixed solvent with a compatible solvent.

Proteins such as collagen or gelatin can be dissolved in the organic fluorine compound such as 1,1,1,3,3,3-hexafluoro-2-propanol (HFIP) or 2,2,2-trifluoroethanol (TFE). Further, even if a HFIP solution containing gelatin is placed at 4° C., gel is not formed. Therefore, handling is easy even in highly reactive reaction.

Exampled of the chemical modification in the present invention may include cross-linking of biopolymer or polypeptide, and introduction of a functional group into biopolymer or polypeptide.

Cross-linking of biopolymer or polypeptide can be carried out using a crosslinking agent. A crosslinking agent used in the present invention is not particularly limited as long as the present invention can be carried out. It may be a chemical crosslinking agent or an enzyme, and a chemical condensing agent is particularly preferred. Examples of a crosslinking agent include formaldehyde, glutaraldehyde, carbodiimide, cyanamide, vinyl sulfone, and diepoxide. Preferably, formaldehyde and glutaraldehyde can be used. It is desirable to use a solvent that is less nucleophilic than water for protein condensation. Although HFIP and TFE are alcohols, they have highly acidic hydroxyl groups and are poorly nucleophilic. Therefore, it is thought that such a solvent is less likely to inhibit a reaction involving nucleophilic attack.

When the present invention is applied to the introduction of a functional group into biopolymer, the biopolymer is reacted with a compound having a desired functional group together with a condensing agent, or is reacted with acid anhydride, acid chloride, or epoxide, each having a desired functional group. The aforementioned crosslinking agent is preferably used as the condensing agent. The compound used in the present invention is not particularly limited. A compound having a highly hydrophobic functional group or a functional group which causes degradation or reaction by alkali is preferred in order to achieve the object of the present invention. Preferred compound is a compound having an ester group, an amide group, a dithiocarbamyl group, a carbonate ester group, an epoxide group, or α-orthoester group, or a compound having α, β unsaturated bond. Examples thereof include 2-N,N-diethyldithiocarbamylmethyl benzoate, 3-N,N-diethyldithiocarbamylmethyl benzoate, 4-N,N-diethyldithiocarbamylmethyl benzoate, 2-vinyl benzoate, 3-vinyl benzoate, 4-vinyl benzoate, and carboxylated camphorquinone.

Further, examples of the compound used in the chemical modification include acid anhydrides (for example, 2-N,N-diethyldithiocarbamylmethyl benzoate anhydride, 3-N,N-dietyldithiocarbamylmethyl benzoate anhydride, 4-N,N-diethyldithiocarbamylmethyl benzoate anhydride, 2-vinyl benzoate anhydride, 3-vinyl benzoate anhydride, 4-vinyl benzoate anhydride), acid chlorides (2-N,N-diethyldithio carb amylmethyl benzoate chloride, 3-N,N-diethyldithiocarbamylmethyl benzoate chloride, 4-N,N-diethyldithiocarbamylmethyl benzoate chloride, 2-vinyl benzoate chloride, 3-vinyl benzoate chloride, 4-vinyl benzoate chloride), and epoxides.

In the present invention, when biopolymer or polypeptide is chemically modified, the concentration of a condensing agent in the reaction mixture is generally 1.0 to 10% by weight, and is preferably 1.0 to 5.0% by weight.

The chemical modification of biopolymer involves two steps of mixing a solution of biopolymer with a reaction substrate, and performing a reaction of the thus obtained homogenous solution.

In the present invention, the temperature for mixing a biopolymer with a reaction substrate is not particularly limited as long as the obtained solution can be uniformly stirred. However, the temperature is preferably 0° C. to 40° C., more preferably 0° C. to 30° C., further preferably 3° C. to 25° C., even more preferably 3° C. to 15° C., yet more preferably 3° C. to 10° C., and particularly preferably 3° C. to 7° C.

After stirring a biopolymer and a reaction substrate, it is possible to raise the temperature. The reaction temperature is not particularly limited as long as the reaction proceeds. However, in view of biopolymer degeneration or degradation, the reaction temperature is substantially 0° C. to 60° C., preferably 0° C. to 40° C., more preferably 3° C. to 25° C., further preferably 3° C. to 15° C., even more preferably 3° C. to 10° C., and particularly preferably 3° C. to 7° C.

The form of the structure of a chemically modified (crosslinking, or introduction of a functional group) biopolymer or polypeptide which is obtained by the present invention is not particularly limited. Examples of the form include sponge, film, non-woven fabric, fibers (tubes), and particles. The structure can be used in any form. Examples of such form include pyramidal, conical, rectangular cylindrical, circular cylindrical, spherical, and spindle-shaped structure, and structure produced by using molds with any desired shapes. Preferably, the form is a rectangular cylindrical, circular cylindrical, or spindle-shaped structure, or a structure produced using a mold with any desired shape. More preferably, the form is a pyramidal, conical, rectangular cylindrical, or circular cylindrical structure. Most preferably, the form is a rectangular cylindrical or circular cylindrical structure.

The size of the structure is not particularly limited. When the structure is in the form of sponge or non-woven fabric, the size is preferably 500 centimeters square or less, preferably 100 centimeters square or less, particularly preferably 50 centimeters square or less, and most preferably 10 centimeters square or less. When it is formed into a fiber (tube), the diameter of a fiber or tube (or one side of the cross section thereof) is 1 nm or more and 10 cm or less, preferably 1 nm or more and 1 cm or less, more preferably 1 nm or more and 100 μmore less, particularly preferably 1 nm or more and 1 μm or less, and most preferably 1 nm or more and 10 nm or less. In addition, the length thereof is not particularly limited. The length thereof is preferably 10 μm or more and 100 m or less, more preferably 100 μmore more and 10 m or less, further preferably 1 mm or more and 1 m or less, and most preferably 1 cm or more and 30 cm or less. When the structure is in the form of particles, the particle size (diameter) preferably ranges from 1 nm to 1 mm, more preferably ranges from 10 nm to 200 μm, further preferably ranges from 50 nm to 100 μm, and particularly preferably ranges from 100 nm to 10 μm.

The thickness of the structure is not particularly limited. The thickness is preferably 1 nm or more, more preferably 10 nm or more, further preferably 100 nm or more, even more preferably 1 μm or more, yet more preferably 10 μm or more, and most preferably 100 μm or more.

It is possible to add an additive to the chemically modified biopolymer or polypeptide which is produced by the method of the present invention according to need. Examples of additives include drugs, pigments, softening agents, transdermal-absorption-promoting agents, moisturizing agents, thickening agents, surfactants, preservatives, aroma chemicals, and pH adjusters.

The chemically modified biopolymer or polypeptide which is produced by the present invention may incorporate a drug therein, and may be used. Specific examples of such drugs include anticancer agents (e.g., paclitaxel, Topotecin, taxotere, 5-fluorouracil, and cisplatin), immunosuppressive agents (e.g., Rapamycin, tacrolimus, and cyclosporine), anti-inflammatory agents, antithrombotic agents, antipsychotic agents (e.g., amitriptyline hydrochloride), antidepressants, antioxidants, antiallergic agents, growth factors (e.g., fibroblast growth factors, epithelial cell growth factors, insulin-like growth factors, transforming growth factors, vascular endothelial cell growth factors, hepatocellular growth factors, platelet-derived growth factors, nerve growth factors), hormones, supplement components, and cosmetic components.

Applications of the chemically modified biopolymer or polypeptide which is produced by the method of the present invention are not particularly limited. However, it can be used for transdermally absorbable agents, topical therapeutic agents, oral therapeutic agents, injection therapeutic agents, cosmetics, supplements, foods, and pigments. Preferably, it can be used for transdermally absorbable agents, topical therapeutic agents, oral therapeutic agents, and cosmetics. Further preferably, it can be used for transdermally absorbable agents, topical therapeutic agents, and oral therapeutic agents. Most preferably, it can be used for transdermally absorbable agents and topical therapeutic agents.

The chemically modified biopolymer or polypeptide which is produced by the present invention can be used for, for example, skin agents for external use that contain anticancer agents. Examples of diseases to which skin agents for external use can be applied include skin cancer, keratosis, malignant melanoma, mycosis fungoides, breast cancer, prostate cancer, uterine cancer, vaginal cancer, penile cancer, and colon cancer. Preferable examples thereof are skin cancer and keratosis.

The chemically modified biopolymer or polypeptide which is produced by the present invention can be used for materials that are implantable in biotissues. For instance, it is possible to restore a tissue by implanting a crosslinked biopolymer in which cells are embedded in a lesion site. In another embodiment, it is possible to restore a tissue by implanting a crosslinked biopolymer containing a growth factor or a different pharmaceutical agent in a biotissue.

Types of cells to be contained in the chemically modified biopolymer or polypeptide are not particularly limited. However, examples thereof include myelocytes, embryonic stem cells, adult stem cells, chondrocytes, osteoblasts, fibroblasts, vascular endothelial cells, vascular smooth muscle cells, cardiomyocytes, and epithelial cells.

Body parts that are required to have particular strength, to which a material that is implantable in a biotissue is applied, are bones, cartilages, hearts, blood vessels, and the like.

In another embodiment, a material that is implantable in a biotissue can be used for coating of medical products used in vivo such as artificial blood vessels, artificial organs such as artificial hearts, and stents used for blood vessel treatment. When such a material is used for a stent, the stent surface can be coated with a crosslinked biopolymer containing an anticancer agent or an immunosuppressive agent.

The method of the present invention is available, even if a compound which is not modified is not dissolved in the organic fluorine compound. Namely, efficiency becomes worse in the chemical modification in water system so that highly efficient introduction of a compound cannot be achieved, but a compound can be dissolved in the organic fluorine compound by means of introduction of a hydrophobic compound. In such a case, a reaction for introduction of a compound is carried out in water system in the first step, and chemical reaction using an organic fluorine compound is carried out in the second step. Thus, it becomes possible to introduce a hydrophobic compound into biopolymer or polypeptide at high efficiency.

The present invention is hereafter described in greater detail with reference to the following examples, although the scope of the present invention is not limited thereto.

EXAMPLES

Example 1

Chemical Modification of Gelatin by a Hydrophobic Compound (Dithiocarbamylation)

2,2,2-trifluoroethanol solution (6 mL) containing water soluble carbodiimide (WSC) (223 mg) as a condensing agent and 4-dithiocarbamylmethyl benzoate (165 mg) was stirred at 0° C. for 1 hour. Then, the obtained solution was added to TFE solution (6 mL) containing gelatin (PSK gelatin, Nippi, 300 mg), 57 mg of N-hydroxysuccinimide (NHS) and 60 mg of dimethylaminopyridine (DMAP) at room temperature. The obtained solution was stirred one day. The solution was filtered, and was diluted with water. The filtrate was dialyzed for 3 days (Dialysis Membrane 36, Wako Pure Chemical Industries, Ltd.), and was freeze-dried. The amount of dithiocarbamyl group which was introduced was calculated by measuring absorbance at 280 nm of the obtained freeze-dried product by UV-visible spectrum. As a result, it was found that a gelatin was obtained where 85% of the amino groups was dithiocarbamylated.

On the other hand, by the method described in Journal of Biomaterial Science, Polymer Edition 16(7) 809-827, 2005 (Non-Patent Document 1), 4-dithiocarbamylmethyl benzoate (165 mg) was dissolved in 1 N sodium hydroxide aqueous solution, and the solution was neutralized by 1 N hydrochloric acid to be pH8. The solution was added to PBS solution containing WSC (6 ml), and the mixture was stirred at 0° C. for 1 hour. The obtained solution was added PBS solution (6 mL) containing gelatin (3 g), and the mixture was stirred one day at room temperature. As to the pH of the reaction solution, pH8 and pH10 were studied. The obtained suspension was filtered, dialyzed and then freeze-dried. The amount of dithiocarbamyl group was measured in the same way as mentioned above. As a result, it was 12% in the reaction solution of pH8, and 75% in the reaction solution of pH10. Thiol groups were detected in the dithiocarbamylated gelatin which was obtained by the reaction at pH10, which suggests that a part of the introduced dithiocarbamyl groups was hydrolyzed.

By using TFE for the introduction of a functional group into gelatin side chain, introduction of a highly hydrophobic compound, which was difficult in a water system, becomes easy, and introduction of a functional group which is subjected to degradation by alkali becomes possible.

The cLogP value of 4-dithiocarbamylmethyl benzoate is 3.6, and this compound is hydrophobic. The dithiocarbamyl group is a functional group which is degraded by alkali so as to produce thiol.

Example 2

Cross-linking of Gelatin Using Hydrophobic Terephthalic Acid

A HFIP solution (1 mL) containing 38.4 mg (twice molar amounts of terephthalic acid) of WSC (DOJINDO) and 16.6 mg of terephthalic acid was stirred at 4° C. for 1 hour so as to activate carboxyl group. Then, the obtained solution was added to a TFE solution (2 mL) containing 600 mg of acid-treated gelatin (PSK gelatin, Nippi), 115 mg of N-hydroxysuccinimide and 122 mg of dimethylaminopyridine. The obtained solution was left stand at room temperature for 3 hours, so that the entire solution was hardened like gel.

Example 3

Chemical Modification of Gelatin Using Hydrophobic Compound 2,2,2-trifluoroethanol solution (6 mL) containing WSC (223 mg) and 4-dithiocarbamylmethyl benzoate (165 mg) was stirred at 0° C. for 1 hour. Then, the obtained solution was added to TFE-HFIP mixed solution (6 mL, TFE/HFIP=5) containing gelatin (PSK gelatin, Nippi, 300 mg), 57 mg of N-hydroxysuccinimide (NHS) and 60 mg of dimethylaminopyridine (DMAP) at room temperature. The obtained solution was stirred one day. The solution was filtered, and was diluted with water. The filtrate was dialyzed for 3 days (Dialysis Membrane 36, Wako Pure Chemical Industries, Ltd.), and was freeze-dried. The amount of dithiocarbamyl group which was introduced was calculated by measuring absorbance at 280 nm of the obtained freeze-dried product by UV-visible spectrum. As a result, it was found that a gelatin was obtained where 75% of the amino groups was dithiocarbamylated.

The invention claimed is:

1. A method for producing a chemically modified biopolymer or polypeptide, the method comprising:
   chemically modifying a biopolymer or polypeptide in a reaction solution containing an organic fluorine compound, wherein the organic fluorine compound is an alcohol or a ketone,
   wherein the chemical modification is (i) a chemical modification which is made via amide bond, ester bond, ether bond or urethane bond, (ii) an intermolecular cross-linking reaction, or (iii) an intramolecular cross-linking reaction,
   wherein the biopolymer or polypeptide is reacted with at least one compound (A) selected from the group consisting of an acid anhydride, an acid chloride and an epoxide, each having a predetermined functional group, and a compound having a dithiocarbamyl group, to introduce the functional group or the dithiocarbamyl group to the biopolymer or polypeptide, and/or
   the biopolymer or polypeptide is reacted with a crosslinking agent (B) to crosslink the biopolymer or polypeptide, wherein the crosslinking agent is at least one selected from the group consisting of formaldehyde, glutaraldehyde, carbodiimide, cyanamide, vinyl sulfone, terephthalic acid and diepoxide, and
   wherein the biopolymer is selected from the group consisting of a protein and a polysaccharide.

2. The method according to claim 1, wherein the biopolymer is a protein.

3. The method according to claim 1, wherein the biopolymer comprises at least one selected from the group consisting of collagen, gelatin, albumin, laminin, casein, fibroin, fibrin, fibronectin, vitronectin, urokinase, thrombomodulin, and antithrombin III.

4. The method according to claim 2, wherein the protein is a human, bovine, pig, fish or plant protein, or a gene recombinant protein.

5. The method according to claim 1, wherein said at least one compound (A) is a compound having an acid anhydride group, an epoxide group, or a dithiocarbamyl group.

6. The method according to claim 1, wherein the crosslinking agent (B) is a condensing agent.

7. The method according to claim 1, wherein the organic fluorine compound has a carbon number of 1 to 8.

8. The method according to claim 1, wherein the organic fluorine compound is 2,2,2-trifluoroethanol, 1,1,1,3,3,3-hexafluoro-2-propanol, or hexafluoroacetone.

9. The method according to claim 1, wherein the organic fluorine compound is 2,2,2-trifluoroethanol.

10. The method according to claim 1, wherein said at least one compound (A) is selected from the group consisting of 2-N,N-diethyldithiocarbamylmethyl benzoate, 3-N,N-diethyldithiocarbamylmethyl benzoate, 4-N,N-diethyldithiocarbamylmethyl benzoate, 4-dithiocarbamylmethyl benzoate, 2-N,N-diethyldithiocarbamylmethyl benzoate anhydride, 3-N,N-diethyldithiocarbamylmethyl benzoate anhydride, 4-N,N-diethyldithiocarbamylmethyl benzoate anhydride, 2-vinyl benzoate anhydride, 3-vinyl benzoate anhydride, 4-vinyl benzoate anhydride, 2-N,N-diethyldithiocarbamylmethyl benzoate chloride, 3-N,N-diethyldithiocarbamylmethyl benzoate chloride, 4-N,N-diethyldithiocarbamylmethyl benzoate chloride, 2-vinyl benzoate chloride, 3-vinyl benzoate chloride, 4-vinyl benzoate chloride, and epoxides, and
    the crosslinking agent (B) is at least one selected from the group consisting of formaldehyde, glutaraldehyde, carbodiimide, cyanamide, vinyl sulfone, terephthalic acid and diepoxide.

* * * * *